(12) United States Patent
Rempt et al.

(10) Patent No.: US 7,542,871 B2
(45) Date of Patent: Jun. 2, 2009

(54) CONTROL FOR HAND-HELD IMAGING ARRAY USING COMPUTER MOUSE CONFIGURATION

(75) Inventors: Raymond D. Rempt, Woodinville, WA (US); Daniel J. Wright, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 18 days.

(21) Appl. No.: 11/163,785

(22) Filed: Oct. 31, 2005

(65) Prior Publication Data

US 2007/0100579 A1    May 3, 2007

(51) Int. Cl.
*G06F 15/00* (2006.01)
(52) U.S. Cl. .................................................. 702/168
(58) Field of Classification Search ................. 702/168, 702/167
See application file for complete search history.

(56) References Cited

U.S. PATENT DOCUMENTS

| | | | |
|---|---|---|---|
| 5,343,750 A * | 9/1994 | Bashyam ..................... | 73/635 |
| 5,549,004 A * | 8/1996 | Nugent ........................ | 73/622 |
| 6,150,809 A | 11/2000 | Tiernan et al. | |
| 2004/0004475 A1 * | 1/2004 | Goldfine et al. ............. | 324/242 |
| 2004/0055171 A1 * | 3/2004 | Toom .......................... | 33/533 |
| 2005/0212514 A1 * | 9/2005 | Saka et al. .................. | 324/222 |
| 2006/0017937 A1 * | 1/2006 | Vaccaro et al. ............. | 356/607 |

OTHER PUBLICATIONS http://en.wikipedia.org/wiki/Magnetic_field, p. 1-9.*
http://en.wikipedia.org/wiki/Eddy_current, p. 1-2.*

* cited by examiner

*Primary Examiner*—Tung S Lau
(74) *Attorney, Agent, or Firm*—Felix L. Fischer

(57) ABSTRACT

A hand held non-destructive testing device has a frame which supports an NDI sensor and incorporates means for translation across a surface to be inspected with position registration and resilient means for maintaining the sensor and the translation means in intimate contact with the surface. An ergonomic handle is mounted to the frame for manually controlled translation of the frame incorporates a plurality of control means for control of the sensor in scanning of the surface under inspection.

10 Claims, 5 Drawing Sheets

CONTROL FOR HAND-HELD IMAGING ARRAY USING COMPUTER MOUSE CONFIGURATION

DEVELOPMENT UNDER GOVERNMENT CONTRACT

This invention was made with Government support under contract number N00014-04-C-0182 awarded by the United States Navy Office of Naval Research. The government has certain rights in this invention.

REFERENCE TO RELATED APPLICATIONS

This patent application is related to copending application Ser. No. 11/163,834 filed Nov. 1, 2005 entitled "FLEXIBLE HAND HELD MR SCANNING ARRAY FOR CRACKS/FLAWS" having a common inventor and a common assignee with the present application, the disclosure of which is incorporated herein by reference.

BACKGROUND OF THE INVENTION

1. Field of the Invention

This invention relates generally to the field of non-destructive inspection (NDI) of structures and more particularly to a hand held positioning and control device for imaging arrays such as Magnetoresistive (MR) scanning arrays.

2. Description of the Related Art

Non-destructive inspection (NDI) of aerospace structures to detect flaws may be performed by various techniques that include X-ray radiography, ultrasonics, acoustic emissions, and eddy currents. Current imaging scanners are typically operated using mechanical positioning means which require significant mechanical and structural support. Currently there is no hand held device that can rapidly scan along a row of fasteners to inspect the subsurface condition of the structure.

Eddy current inspection devices are commonly used for NDI of electrically conductive components. Eddy current inspection devices typically use one or more excitation coils to generate an alternating magnetic field, which in turn induces eddy currents in the component, and typically use a pickup coil to detect the magnetic field generated by the eddy currents. When an eddy current encounters an internal flaw of the component, the eddy current flows around the flaw and the resulting magnetic field generated by the eddy current is changed. The pickup coil indirectly detects this change which gives information regarding the location and size of the flaw within the component.

Magnetoresistive (MR) sensors are known for low frequency performance permitting deep feature/flaw detection in metallic structure at sensitivities considerably above those provided by conventional eddy current techniques. Exemplary NDI systems employing MR are disclosed in U.S. Pat. No. 6,150,809 to Tiernan et al. which uses two parallel sheets of conductors to create the magnetic field and uses a giant magnetoresistive (GMR) sensor positioned between the sheets to detect the magnetic field signals generated by eddy currents and application Ser. No. 10/923,519 entitled EDDY CURRENT INSPECTION DEVICE, having a common assignee with the present invention, the disclosure of which is incorporated herein by reference.

Eddy current inspection using MR sensors is applicable to scanning of specific structural elements on an aircraft, containing rows of rivets or other fasteners. It is therefore desirable that an imaging scanner be mounted in a structure for operation by hand to allow a technician to accurately yet conveniently perform inspection of the desired structure.

SUMMARY OF THE INVENTION

A system incorporating the present invention provides a non-destructive testing device having a frame incorporating means for translation across a curved surface to be inspected with resilient means for maintaining a non-destructive inspection (NDI) sensor and the translation means in intimate contact with the surface. An ergonomic handle mounted to the frame for manually controlled translation of the frame incorporates at least one control means for control of the sensor in scanning of the surface under inspection.

In an exemplary embodiment, an excitation coil with a plurality of conductor ribbons is attached to a flexible membrane. The frame supports the membrane and provides the means for translation across a surface to be inspected and resilient means for maintaining the entire membrane surface with the excitation coil and the translation means in intimate contact with the surface. A magnetoresitive (MR) array is supported within the frame adjacent the membrane to be in close proximity to the surface. The MR array detects the magnetic fields resulting from eddy currents created by the excitation coil for identification of cracks or other features of interest in the surface under inspection.

Flexibility of the membrane and excitation coil allows inspection of curved surfaces not possible with rigid excitation devices.

BRIEF DESCRIPTION OF THE DRAWINGS

These and other features and advantages of the present invention will be better understood by reference to the following detailed description when considered in connection with the accompanying drawings wherein.

DETAILED DESCRIPTION OF THE INVENTION

Figure 1:
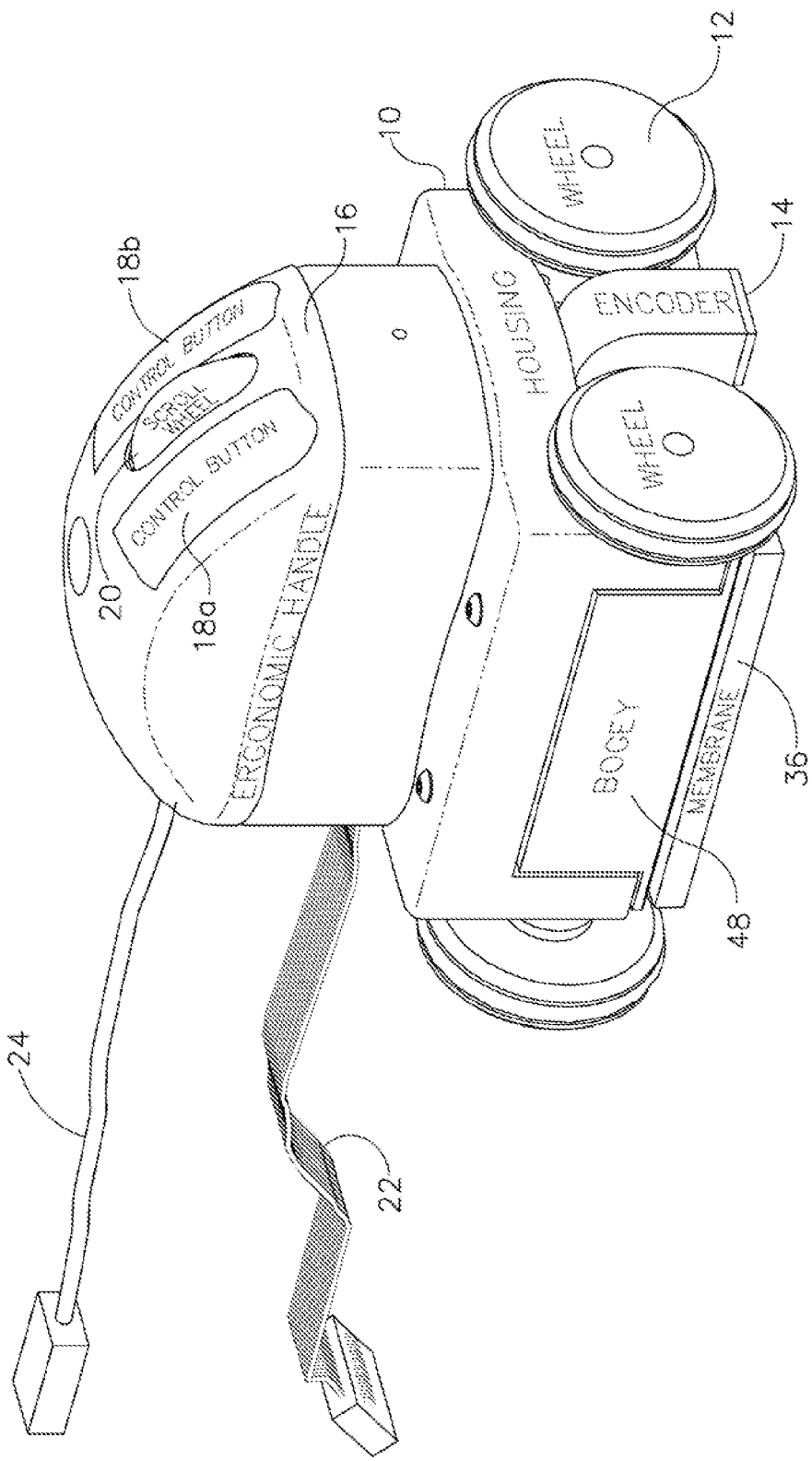
FIG. 1 is an isometric external view of an embodiment of the invention.

The present invention provides the capability to scan the surface of a structure using a hand held NDI device with integral controls. FIG. 1 shows details of an exemplary embodiment. A housing 10 encloses the elements of the scanner, which will be described for an exemplary embodiment in greater detail subsequently. Wheels 12 are mounted to a frame of the housing for translating the scanner in a desired direction by the operator. A position encoder 14 such as an encoder wheel, optical sensor or track ball is mounted from the frame of the housing intermediate the wheels for continuous position registration. Manual operation of the sensing device is enhanced with a "mouse" like handle 16 mounted to the frame. Integral control buttons 18a and 18b and scroll wheel 20 provide for control of the sensor and operational functions of the complete unit. The mouse handle is shaped ergonomically so that an operator can easily cause the device to glide across the surface of the aircraft being inspected.

For the embodiment shown, connecting ribbon cable 22 operably provides power and data communication between the sensor and external electronics while an additional cable 24 provides connection to the control elements and position encoder. Those skilled in the art will recognize alternative cabling arrangements as may be most desirable for the type of scanner employed.

Figure 2:
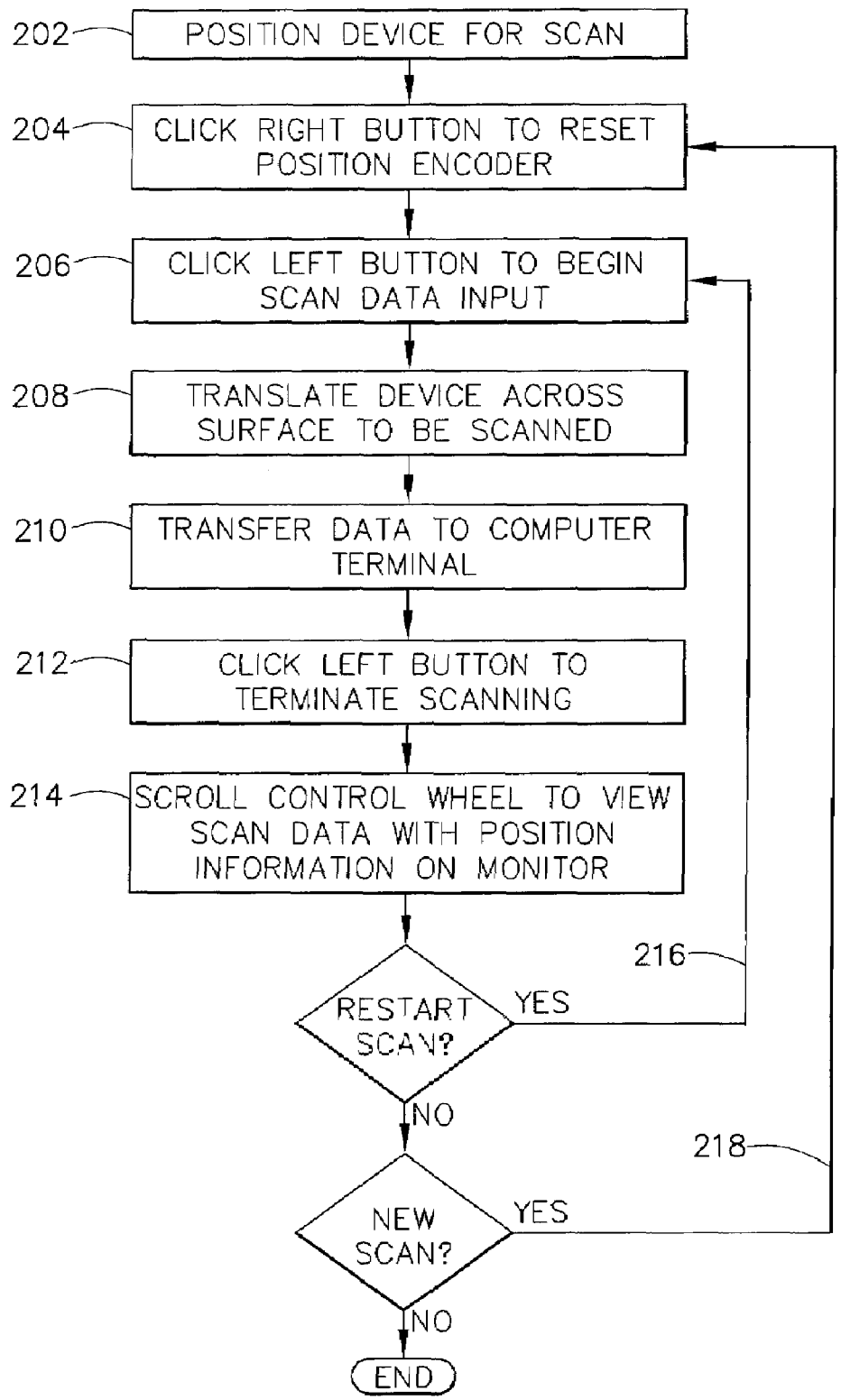
FIG. 2 is a flow chart of exemplary operational sequence for NDI using the controls provided by the embodiment of the invention disclosed in FIG. 1

For operation of the functions typically required in NDI scanner operation, the controls provided by the present invention allow the operator to conduct the entire inspection using the controls on the hand held device. As shown in the flow chart of FIG. 2 for an exemplary NDI control sequence, the operator places the device in position for scanning, for example, a row of fasteners 202. By "clicking" the right control button 204, the position defined by the position encoder is reset. By clicking the left control button 206, entry of scan data is initiated. The device is then translated along the fastener row 208. Data from the position encoder and the scanning array are transferred 210 to a computer terminal such as a portable personal computer for data storage, manipulation and visualization. Upon completion of the scan, the operator again clicks the left control button 212 to terminate the scanning. The control wheel is then operable to scroll through the acquired data 214 which is presented on the computer monitor with position from the encoder and visual image from the scanning array presented. If additional scanning is desired 216, the left button is again "clicked" while if a new scan is desired 218, the right button is clicked resetting the scan position.

While an exemplary format for use of the controls is presented herein, the use of mouse type control inputs allows the functionality of the control buttons to be software programmable for a plurality of functions.

Figure 3:
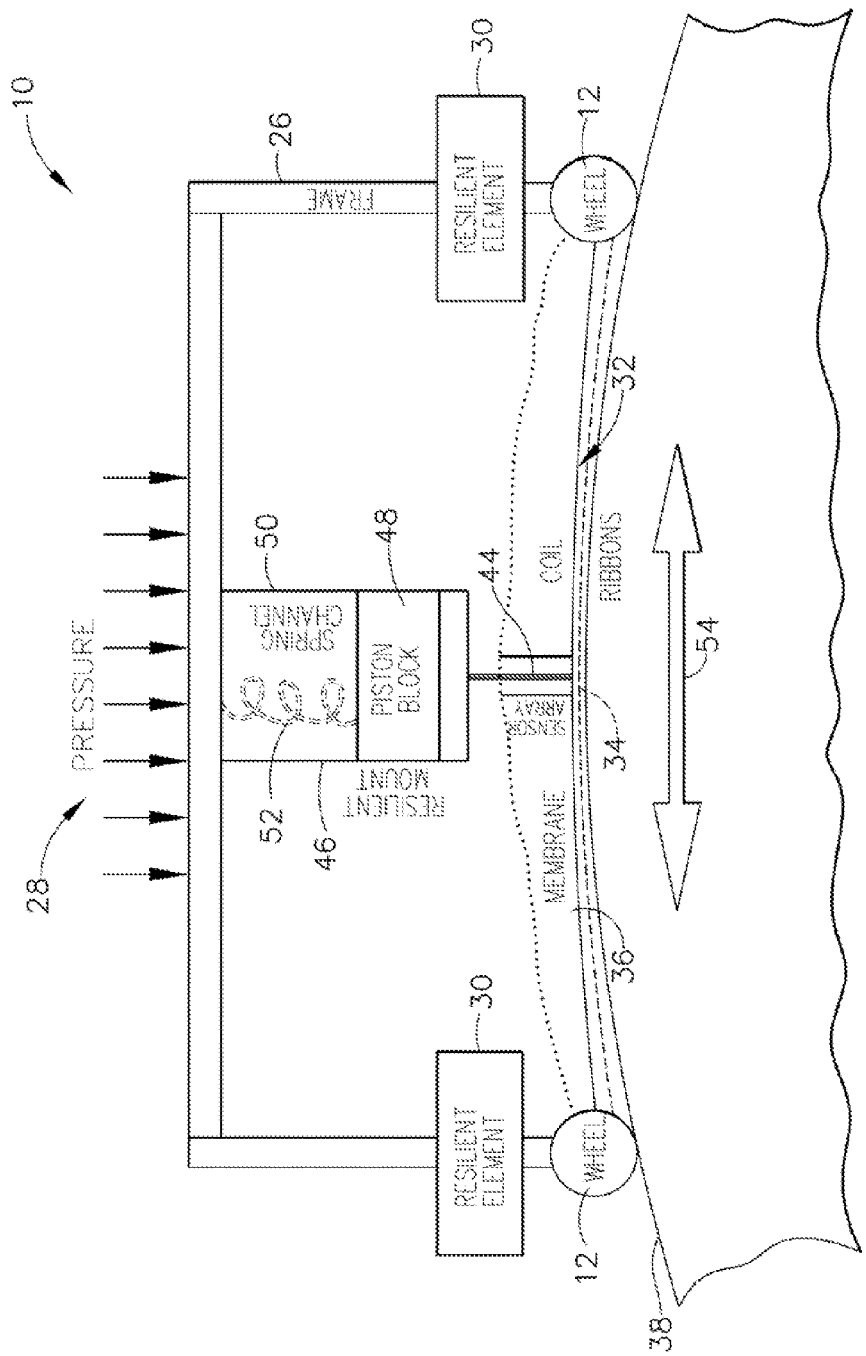
FIG. 3 is a schematic diagram of the elements of the present invention for an embodiment using an MR scanning array.

An embodiment of the present invention for one type of scanner particularly suited to the features of the invention, a magnetoresistive (MR) array, is shown schematically in FIG. 3. A rigid frame 26 provides for transferring downward pressure exerted by the operator, as represented by arrows 28. The frame incorporates resilient structural elements 30 providing spring loads, so that pressure is always applied when the operator presses downward on the mouse handle to intimately position the scanner with respect to the surface under inspection. For the embodiment shown, the displacement range of the resilient elements allows for various radii of curvature in the surface of the item being inspected to be accommodated, while maintaining continuous and total contact between the surface being inspected and a flexible excitation coil 32. The coil, with its conducting ribbons 34 perpendicular to the plane of the drawing in FIG. 3 is shown in a gently curved configuration. The coil is embedded in or mounted on a flexible membrane or pad 36 of rubber or other nonconductive substrate. In an exemplary embodiment medium soft closed cell blended neoprene sponge identified by product number CCNS SCE 41 is employed as the membrane. The surface under inspection 38 is the shape which defines the curved shape of the coil through intimate contact between the coil and membrane and the surface.

Figure 4:
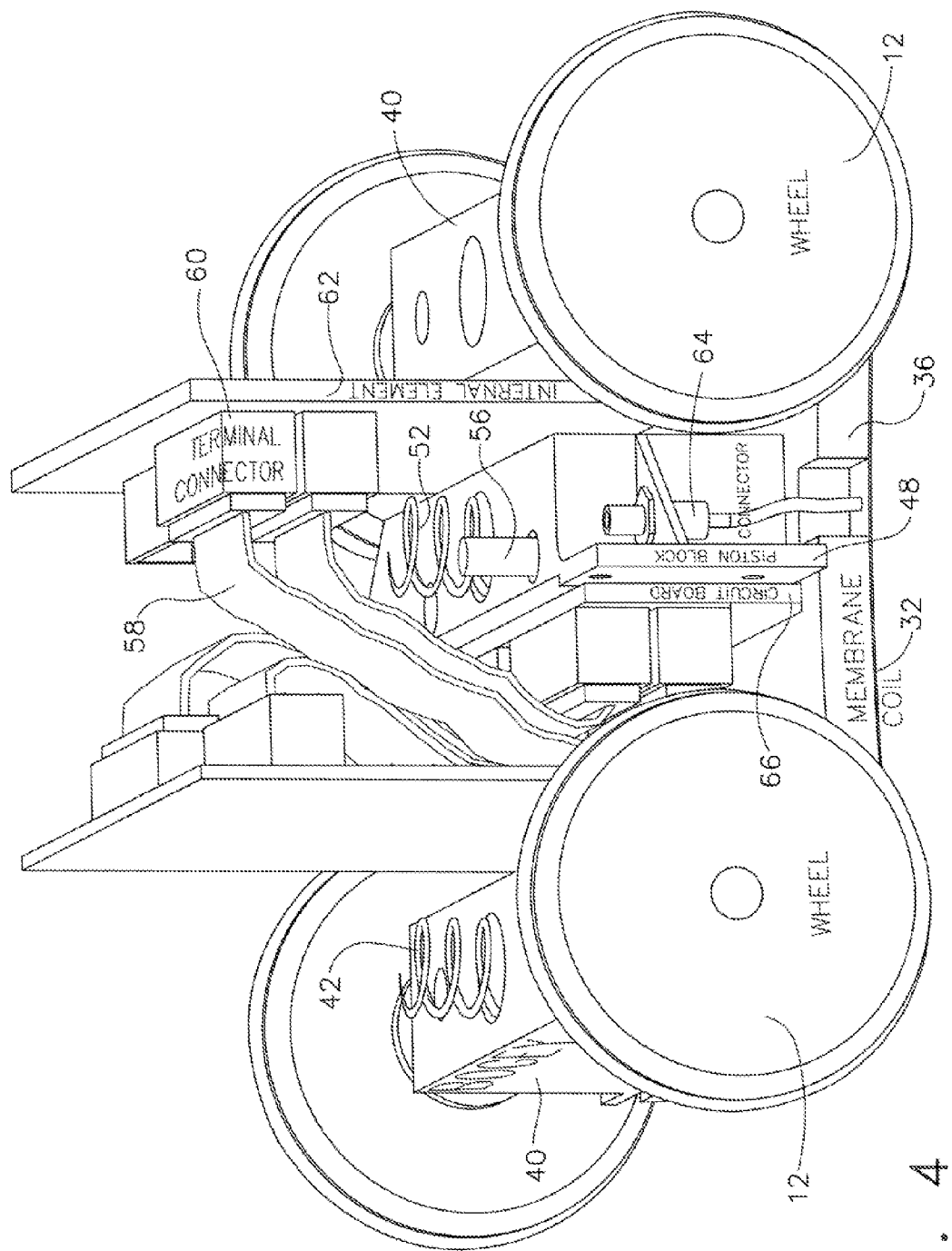
FIG. 4 is an isometric cutaway view of the embodiment of FIG. 1 showing structural details for the MR scanning array application; and, FIG. 5 is an exemplary printed circuit board housing the MR array for use with the disclosed embodiment of the invention.

As shown in FIG. 4, the resilient elements of the frame are provided by the wheel bogeys 40 urging the wheels into intimate contact with the surface under inspection by springs 42 reacting against receivers on the frame. The sensing surface, in the example present in the drawings the membrane, is mounted to the lower surface of the bogeys intermediate the wheels. The diameter of the wheels is predetermined to maintain the intimate contact of the membrane and the excitation coil mounted thereto with the surface undergoing inspection.

As shown schematically in FIG. 3 and a physical embodiment in FIG. 4, sensor array 44 is contained in housing 10. The array is supported by a resilient mount 46 shown as piston or block 48 constrained within a cylinder or channel 50 and loaded by a spring 52. For purposes of description herein, the scan motion is left and right in the configurations shown in FIG. 3 for circumferential scanning as represented by double arrow 54 at the bottom of the figure. Wheels 12 support the housing with respect to the surface under inspection and protrude coincident with or slightly beyond the coil, so that the coil is in contact with the surface as well as the wheels themselves.

The sensor array is mounted to a printed circuit (PC) board, the edge of which is adhesively bonded or otherwise affixed to the excitation coil to assure close contact of the array with the surface under investigation. Block 48 to which the PC board is mounted is urged downward by spring 52 reacting against the frame. Guide rods 56 are employed to retain the block and mounted array in a substantially parallel or tangential orientation with respect to the surface under investigation. The connectors for the array receive ribbon cables 58 for interconnection to a terminal connector 60 mounted on internal element 62 for further connection to the external power and data cable. Power for the excitation coil is provided through connector 64, which for the embodiment shown is attached to slider block 48 which acts as the array holder/fixture.

Figure 5:
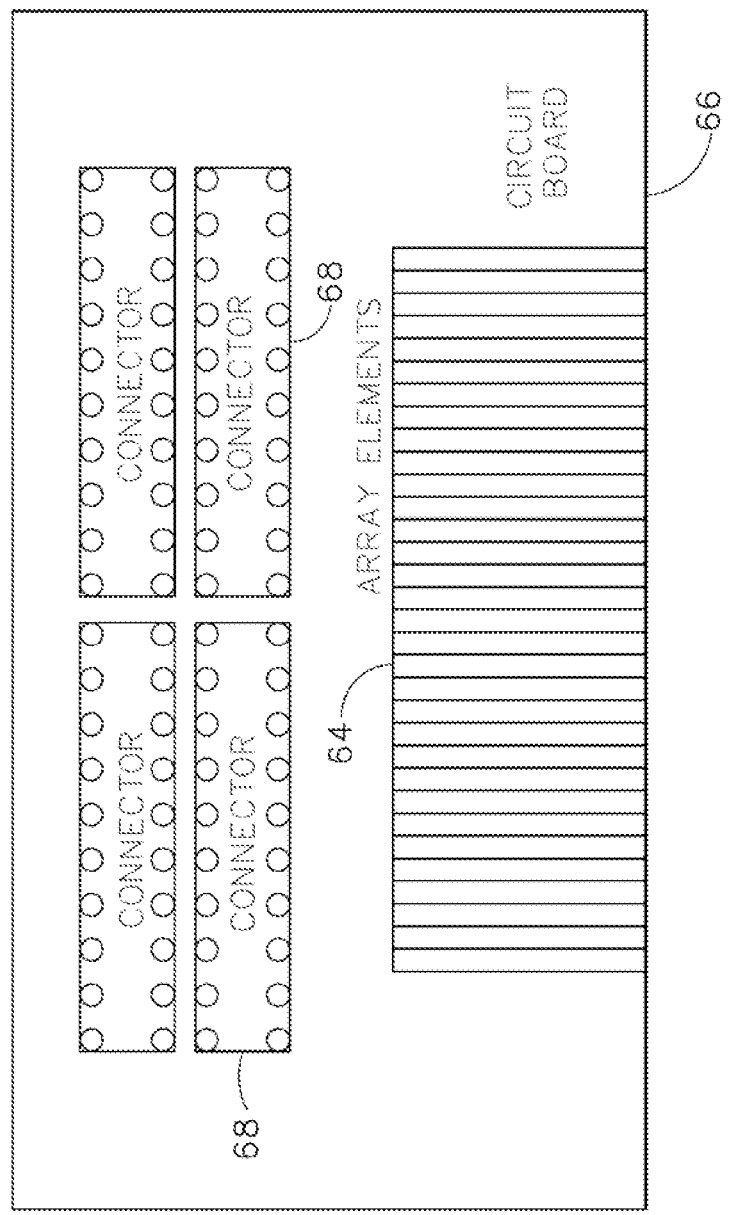

The scanning MR array is shown in FIG. 5. For the embodiment disclosed, the array employs 32 elements 65 oriented along the lower edge of a printed circuit board 66. Multiple connectors 68 provide external connection to the elements through integral wiring on the PC board. Giant Magnetoresistive sensors (GMR) are employed in the embodiment disclosed. Inter-sensor spacings of 0.020 inch and 0.031 inch have been employed in exemplary devices employing the invention.

Alternative embodiments employ anisotropic magnetoresistive (AMR) sensors in staggered arrays and the invention disclosed herein is applicable for use with spin dependent tunneling (SDT) MR sensors for alternative inspection applications.

The embodiment of the invention disclosed with an imaging array of MR sensors provides for inspection of curved surfaces, such as those commonly found on aircraft fuselages and wings. The excitation coil is flexible, and is attached to a piece of flexible material, such as a dense foam rubber. The density and flexibility of this material, to which the coil is affixed, ensures that the coil remains in intimate contact with the top surface of the component undergoing inspection. Downward pressure applied by the operator during the scanning ensures that this contact is continuous, and uninterrupted, and over the entire surface of the coil.

The entire unit is ergonomically constructed, permitting easy hand scanning. As the unit is scanned in the direction indicated, the downward pressure exerted by the operator keeps the flexible membrane mounted excitation coil in contact with the surface of the item being inspected. The MR array is maintained in contact with the surface via the spring which pushes down on the block to which the array PC board is mounted. The array is linearly oriented perpendicular to the plane of FIG. 3 with the sensors sensitive to the field in the direction normal to the surface of the item being inspected. As the unit is scanned over the surface employing the controls as previously described, the field values are recorded, and their image is displayed on a computer monitor.

For the embodiment shown, the orientation and configuration of the scanning head created by the flexible membrane, coil and PC board mounted sensors is such that scanning in an axis directed along the circumference of the curved surface, the full sensor array is always seated such that it is in contact along its full length with the surface being inspected, being above that surface by the thickness of the excitation coil, which is very thin, and a thin insulating layer which may be created using mylar tape or similar material. The configuration shown in the FIG. 3 permits scanning for cracks that are parallel to the circumferential direction.

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. A hand held non-destructive testing device comprising:
a frame supporting an NDI sensor and incorporating
a plurality of wheels mounted to the frame on bogeys for translation across a curved surface to be inspected,
springs intermediate the bogies and the frame for resilient vertical translation of the bogies for maintaining the sensor and the wheels in intimate contact with the surface to be inspected;
an ergonomic handle mounted to the frame for manually holding and controlling translation of the frame, manually compressing the resilient means to maintain intimate contact of the sensor and having at least one control means for control of the sensor in scanning of the surface under inspection;
said NDI sensor having
an excitation coil having a plurality of conductor ribbons attached to a flexible membrane mounted to the frame and deformable responsive to the compressing of the resilient means; and
a magnetoresitive (MR) array supported within the frame proximate the membrane and surface.

2. A hand held non-destructive testing device as defined in claim 1 further comprising means for measurement of translation of the MR array across the surface under inspection.

3. A hand held non-destructive testing device as defined in claim 1 wherein the MR array elements are arranged in a line parallel to the excitation coil conductor ribbons.

4. A hand held non-destructive testing device as defined in claim 1 wherein the conductor ribbons are arranged perpendicular to the direction of translation and wherein the excitation coil provides a unidirectional current sheet.

5. A hand held non-destructive testing device as defined in claim 1 wherein the MR array comprises a plurality of GMR sensors.

6. A hand held non-destructive testing device as defined in claim 5 wherein each sensor has its axis of sensitivity normal to the surface being scanned.

7. A method for non-destructive testing comprising the steps of:
providing a frame with wheels on spring mounted bogeys supporting a NDI sensor incorporating a flexible membrane proximate a surface to be inspected, resiliently supporting a position encoder and the frame having an ergonomic handle mounted to the frame for manually holding and controlling movement of the frame for scanning of the surface under inspection;
clicking a first control button to reset the position defined by the position encoder;
clicking a second button to initiate entry of scan data;
transferring data from the position encoder and the NDI sensor to a computer terminal for data storage, manipulation and visualization;
moving the frame across a curved surface to be inspected;
resiliently maintaining the sensor and the translation means in intimate contact with the surface to be inspected through pressure on the ergonomic handle perpendicular to the surface to conform the flexible membrane to the surface; and
upon completion of the scan, clicking the first control button to terminate the scanning.

8. A method for non-destructive testing as defined in claim 7 further comprising the steps of:
operating a control wheel to scroll through the acquired data;
presenting the data as scrolled on the computer monitor with position from the encoder and visual image from the scanning array.

9. A method for non-destructive testing as defined in claim 8 further comprising the steps of:
determining if additional scanning is desired;
if so, clicking the first button to resume scanning.

10. A method for non-destructive testing as defined in claim 9 further comprising the steps of:
determining if a new scan is desired;
clicking the second button to reset the scan position.

* * * * *